United States Patent [19]

Kiamil et al.

[11] Patent Number: 5,164,421
[45] Date of Patent: Nov. 17, 1992

[54] HYDROPHILIC POLYURETHANE FOAMS

[75] Inventors: Sinan B. Kiamil, Harlow; Ashok L. Patel, Ilford, both of United Kingdom

[73] Assignee: Smith and Nephew Associated Companies plc, United Kingdom

[21] Appl. No.: 727,333

[22] Filed: Jul. 3, 1991

Related U.S. Application Data

[63] Continuation of Ser. No. 626,974, Dec. 13, 1990, abandoned, which is a continuation of Ser. No. 228,987, Aug. 5, 1988, abandoned, which is a continuation of Ser. No. 27,859, Mar. 19, 1987, abandoned.

[30] Foreign Application Priority Data

Mar. 20, 1986 [GB] United Kingdom ............... 8606988

[51] Int. Cl.$^5$ ............... C08G 18/10; C08G 18/48; A61F 13/00; A61L 15/26
[52] U.S. Cl. ............... 521/159; 521/173; 521/174; 521/905; 528/49; 528/59; 528/76; 528/79; 604/358; 604/367; 604/369; 604/372; 604/904
[58] Field of Search ............... 521/159, 173, 174, 905; 528/49, 59, 79, 45; 128/155, 156; 604/358, 367, 369, 372, 904

[56] References Cited

U.S. PATENT DOCUMENTS

| | | | |
|---|---|---|---|
| 3,432,448 | 3/1969 | Sumbeth et al. | 521/174 |
| 3,457,203 | 7/1969 | Cohen et al. | 521/110 |
| 3,463,745 | 8/1969 | Hofrichter et al. | 521/174 |
| 3,669,913 | 6/1972 | Morehouse | 521/112 |
| 3,875,086 | 4/1975 | Ramey et al. | 521/160 |
| 4,028,313 | 6/1977 | Müller et al. | 521/159 |
| 4,132,839 | 2/1979 | Marans et al. | 521/159 |
| 4,738,991 | 4/1988 | Narayan | 528/49 |
| 4,895,883 | 1/1990 | Pedain et al. | 521/159 |
| 4,914,173 | 4/1990 | Ansell | 528/49 |
| 4,950,695 | 8/1990 | Stone | 521/174 |
| 5,017,625 | 5/1991 | Ansell | 521/159 |

FOREIGN PATENT DOCUMENTS

| | | |
|---|---|---|
| 0024524 | 3/1981 | European Pat. Off. |
| 0031207 | 7/1981 | European Pat. Off. |
| 0031650 | 10/1984 | European Pat. Off. |
| 1066759 | 4/1967 | United Kingdom |
| 1360019 | 7/1974 | United Kingdom |
| 1388228 | 3/1975 | United Kingdom |
| 1425548 | 2/1976 | United Kingdom |
| 1429711 | 3/1976 | United Kingdom |
| 1489052 | 10/1977 | United Kingdom |
| 1528612 | 10/1978 | United Kingdom |
| 1562244 | 3/1980 | United Kingdom |
| 1571730 | 7/1980 | United Kingdom |

*Primary Examiner*—John Kight, III
*Assistant Examiner*—Rabon Sergent
*Attorney, Agent, or Firm*—Rosenman & Colin

[57] ABSTRACT

Hydrophilic polyurethane foams containing residues of a polyalkylene glycol monoalkyl or alkaryl ether may be produced by reacting the ether with an isocyanate having a functionality of greater than two and using only stoichiometric amounts or small excesses e.g. up to 12% of weight of water as foaming agent. Methyl, lauryl, cetyl, octylphenyl and nonyl phenyl ethers may be used. The foams are applicable for the manufacture of absorptive devices such as wound dressings, sanitary towels, diapers, incontinence pads or tampons.

55 Claims, No Drawings

HYDROPHILIC POLYURETHANE FOAMS

CROSS-REFERENCE

This is a continuation of Ser. No. 626,974, filed Dec. 13, 1990, now abandoned, which is a continuation of Ser. No. 228,987, filed Aug. 5, 1988, now abandoned, which is a continuation of Ser. No. 027,859, filed Mar. 19, 1987, now abandoned.

The present invention relates to hydrophilic polyurethane foams, reaction products used to prepare these foams, absorptive devices comprising the foams and methods for their preparation.

There have been several proposals in the patent literature to the use of hydrophilic polyurethane foams, for example as an absorbent material, in hygienic and medical absorptive devices such as sanitary towels, tampons, diapers, incontinence pads and wound dressings. Hydrophilic polyurethane foams, however, are usually more expensive than the conventional cellulosic absorbent materials used in such devices and have therefore not been extensively used in commercial absorptive devices. It is known that hydrophilic polyurethane foams can be prepared by a "prepolymer" process in which a hydrophilic prepolymer having isocyanate end groups is mixed and reacted with water. British Patent No. 1,429,711 (see also U.S. Pat. Nos. 3,812,618, 3,812,619, 3,874,694, 3,889,417, 3,928,138, 3,929,574 and 4,137,200) discloses a hydrophilic polyurethane foam which is formed by mixing and reacting with water an isocyanate capped polyoxyethylene glycol prepolymer using a molar ratio of $H_2O$ to NCO groups in the prepolymer of 6.5 to 390:1. Commercial hydrophilic polyurethane foams of this type are known as Hypol foams and are prepared by mixing and reacting with water. Hypol foam prepolymers are available from W. R. Grace. It has been found, however, that such foam prepolymers need to be mixed with a large molar excess of water typically a 100% to 200% by weight of water to obtain satisfactory foams. Such foams, therefore, during their preparation will contain a large amount of excess water which needs to be removed for example by drying. The need to dry these known foams during their preparation tends to make these foams relatively expensive to manufacture.

It has now been discovered that hydrophilic polyurethane foams can be formed from prepolymers which need to be mixed with only a relatively low amount of water.

Accordingly, the present invention provides a hydrophilic polyurethane foam comprising residues derived from a polyalkylene glycol mono alkyl or mono alkaryl ether.

The present invention also provides a hydrophilic polyurethane foam formed by reacting with water the reaction product of polyisocyanate which has a functionality of greater than 2 and polyalkylene glycol mono alkyl or alkaryl ether.

The hydrophilic polyurethane foam of the invention can be formed by mixing the reaction product with a stoichiometric amount of water. It is preferred, however, to form the foam by mixing the reaction product with a low molar excess of water for example 10% by weight of water. It has been found however, that this low molar excess of water can be easily absorbed by the hydrophilic foam.

The hydrophilic polyurethane foam of the invention therefore does not need drying during its preparation and therefore can be more convenient and more economical to prepare than the prior art foams.

Preferred polyalkylene glycol mono alkaryl ethers are those in which the alkylene group is ethylene.

Suitable polyalkylene glycol mono alkyl ethers for forming the reaction product are those in which the alkyl group contains 1 to 20 carbon atoms. Alkylene favoured ethers are those in which the alkyl group is a methyl group. Another class of preferred polyalkylene glycol mono alkyl ethers are those in which the alkyl group contains 10 to 18 carbon atoms, e.g., lauryl or cetyl.

Suitable polyalkylene glycol mono alkaryl ethers include those in which the aryl moeity is phenyl. Preferred ethers are those in which the alkyl moeity contains from 1 to 20 carbon atoms e.g. octyl or nonyl.

The polyalkylene glycol mono alkyl or alkaryl ether can suitably have an average molecular weight of 180 to 6000. Suitable ethers for forming reaction products used to prepare flexible foams of the invention have an average molecular weight of 180 to 1300 and preferably have an average molecular weight of 350 to 1000.

Suitable ethers for forming reaction products used to prepare stiff foams of the invention have an average molecular weight of 1500 to 6000 and preferably have an average molecular weight of 3000 to 5000.

Apt ethers are polyethylene glycol mono lauryl ethers having an average molecular weight of approximately 1090 and 360 known as Brij 35 and Brij 30 respectively available from Honeywell Atlas and polyethylene glycol mono methyl ethers having an average molecular weight of approximately 500 and 5000 known as PEG monomethylether molecular weight 550 and 5000 respectively available from Aldrich Chemicals.

Suitable polyethylene glycol mono nonyl phenyl ethers are commercially available under the Trade names Antarox CO-320 and Antaro Co-990. Apt polyethylene glycol mono nonyl phenyl ethers, having an average molecular weight of approximately 440 and known as Antarox CO-520 and CO-990 respectively available from GAF (Great Britain) Co. Limited.

The polyethylene glycol mono alkyl or alkaryl ether used in the invention will normally contain water. It is preferred, however, that the ether contains less than 1% by weight of water to limit the number of urea groups formed in the reaction with the polyisocyanate.

The polyisocyanate used for forming the reaction product will have a functionality greater than 2 for example 2 to 5 and will preferably have a functionality of 2.2 to 3.5. Suitable polyisocyanates include aliphatic and aromatic polyisocyanates. Preferred polyisocyanates are aliphatic polyisocyanates. Aliphatic polyisocyanates are usually liquid at ambient room temperature and therefore are convenient to use in a liquid reaction mixture. An apt aliphatic polyisocyanate for use in the invention is a biuret of 1,6 hexamethylene diisocyanate which has a functionality of 2.6 known as Desmodur N100 available from Bayer A.G.

Favoured aromatic polyisocyanates for forming the reaction product are polymeric methylene diisocyanates. Polymeric methylene di isocyanates comprise a mixture of 4,4'-diphenyl methane diisocyanates and one or more of polymeric homologues. Apt polymeric methylene diisocyanates are known as suprasec VM 20, VM 50, DND and VM 90 available from ICI and have a functionality of 2.13, 2.49, 2.70 and 2.90 respectively.

The reaction product suitable for use in the invention can be a reaction product of one or more polyisocyanates and one or more polyalkylene glycol mono alkyl or aryl alkyl ethers, including mixed alkyl and alkaryl ethers. The reaction product may advantageously be formed using a chain extender.

Suitable chain extenders for use in forming the reaction product include ethane diol, 1,3 propane diol and 1,4 butane diol.

Favoured reaction products for use in the invention comprise a reaction product of an aliphatic polyisocyanate and a polyethylene glycol mono alkyl ether in which the alkyl group contains 1 carbon atom or 10 to 18 carbon atoms or a polyethylene glycol mono alkaryl ether in which the alkyl group contains 8 or 9 carbon atoms and the aryl group is phenyl. Further favoured reaction products are a reaction product of a mixture of aliphatic and an aromatic polyisocyanates and one or more of the above mentioned polyglycol mono ethers and optionally a diol chain extender such as 1,4 butane diol.

In another aspect the invention comprises a reaction product of an aliphatic polyisocyanate and a polyethylene glycol mono alkyl ether in which the alkyl group contains 10 to 18 carbon atoms.

It has been found that the reaction product of the invention can advantageously be reacted with water to form a foam without the need for a catalyst.

A similar advantage has also been found with reaction products of aliphatic polyisocyanate and a polyethylene glycol mono octyl phenyl or nonyl phenyl ether.

The use of an aliphatic polyisocyanate in the formation of the reaction product used in the invention has the advantage that the reaction product and foams prepared therefrom are less coloured and more stable to light than those formed from an aromatic isocyanate.

Apt reaction products for use in the invention comprise a reaction product of a biuret of 1,6 hexamethylene diisocyanate and polyethyleneglycol mono lauryl ether, polyethyleneglycol mono methyl ether or polyethylene glycol mono nonyl phenyl ether.

The reaction product used in the invention will contain isocyanate end groups. The reaction product therefore will have an average isocyanate functionality of greater than 1 for example 1.2 to 4 and will preferably have a functionality of 1.5 to 3.5.

The reaction product can be reacted with water to form a hydrophilic polyurethane foam of the invention. The hydrophilic polyurethane so formed will normally be a cross-linked hydrophilic polyurethane foam. The foam polymer will comprise hydrophilic blocks containing urea groups and hydrophilic blocks containing oxyethylene groups. It is believed that the hydrophobic blocks form part of the foam polymer main chains and that the hydrophilic blocks form part of chains which are pendant to the polymer main chain. The hydrophilic polyurethane foam can optionally comprise hydrophobic polyester blocks to increase the strength of the foam as will hereinafter be described.

Varying the relative proportions of hydrophilic and hydrophobic blocks in the polymer molecule can provide the hydrophilic polyurethane foams of the invention with a wide range of water absorption properties. It has been found that the water absorption of the hydrophilic polyurethane foams can range from 25% to 95% by weight of polymer. Preferred hydrophilic polyurethane foams of the invention, however, have a water absorption of 50% to 92% by weight of polymer.

The water absorption of the foam can be obtained by weighing a 1 cm cube of the foam, then immersing the foam in water for 24 hours, removing excessive water by lightly blotting the foam with absorbent paper and then re-weighing the foam cube. The water absorption of the foam (% by weight) can then be calculated as $$\frac{\left[\begin{array}{c}\text{weight of wet} \\ \text{foam (g)}\end{array} - \begin{array}{c}\text{weight of dry} \\ \text{foam (g)}\end{array}\right] \times 100}{\text{weight of wet foam (g)}}$$

The hydrophilic polyurethane foams of the invention can range in properties from flexible foams to stiff foams which can be permanently compressed. The flexibility of the foam, however, can depend on the number of oxyethylene groups in the hydrophilic blocks of the polymer. Flexible hydrophilic polyurethane foams of the invention normally comprise a polymer which has 4 to 30 oxyethylene groups in its hydrophilic blocks and preferably comprise a polymer which has 8 to 25 oxyethylene groups in its hydrophilic blocks.

Stiff foams of the inventions can suitably comprise a polymer which has 35 to 140 oxyethylene groups in its hydrophilic blocks and preferably comprise a polymer which has 70 to 120 oxyethylene groups in its hydrophilic blocks.

Stiff foams of the invention are capable of being compressed into a compressed form. Such compressed forms in contact with water will normally expand to a thickness greater than their uncompressed thickness.

The hydrophilic polyurethane foam of the invention will normally be an open cell foam. The open cell foam can suitably have a density of 20 to 350 Kg/m$^3$ and can preferably have a density of 4 to 150 Kg/m$^3$.

The hydrophilic polyurethane foam can be in a sheet, moulded or particulate form.

The hydrophilic polyurethane foams of the invention can be used in absorptive devices for example as an absorbent component thereof.

In another aspect the present invention provides an absorptive device which comprises a hydrophilic polyurethane foam of the invention. The absorptive device of the invention is preferably a medical or hygienic device such as a wound dressing, sanitary towel, diaper, incontinence pad, tampon or the alike.

In a further aspect the invention provides a process for preparing a hydrophilic polyurethane foam of the invention which comprises reacting with water a reaction product of at least one polyisocyanate which has a functionality of greater than 2 and at least one and polyethylene glycol mono alkyl or alkaryl ether.

The process of the invention has the advantage that the amount of water needed in the reaction can be a stoichiometric amount of water or a low molar excess of water for example 10% by weight which can be easily absorbed by the hydrophilic polyurethane foam thus eliminating the need for a drying step in the process.

Suitable reaction products of a polyisocyanate and a polyethylene glycol mono alkyl or alkaryl ether can be those hereinbefore described in relation to the hydrophilic polyurethane of the invention.

The reaction product used in the process of the invention can be prepared by mixing in a suitable container the required amounts of the polyisocyanate, the polyethylene glycol mono alkyl or alkaryl ether and catalyst such as 0.2% by weight dibutyl tin dilaurate. The mixture, however, may be heated to liquify a solid or semisolid component.

The polyethylene glycol mono alkyl or alkyl aryl ether reactant will normally be pre-dried to a water content of less than 1% by weight. The molar ratio of NCO to OH groups of the reactants used in the reaction including residual or added water is desirably 2.2:1 to 5:1 and is preferably 2.5:1 to 4:1.

Hydrophilic polyurethane foams of the invention can then by simply prepared by mixing the reaction product in liquid form with a suitable amount of water or a material that releases water when heated, as hereinafter described, and if necessary a suitable catalyst, and allowing the mixture to foam and set. It has been found that a suitable amount of water can be the stoichiometric amount of water needed to react with NCO groups in the reaction product. It is preferred, however, in order to obtain a homogenous mixture of water and the reaction product to use up to 12% e.g. 6 to 12% by weight of water and preferably 10% by weight of water in the process.

A suitable catalyst for the reaction is an alkali metal carbonate such as potassium carbonate which can be present in amounts of 0.5 to 1.5% by weight of the reaction product. Reaction products of an aliphatic polyisocyanate and a polyethylene glycol mono alkyl ether in which the alkyl group contains 10 to 18 carbon atoms or a polyethylene glycol mono alkaryl ether in which the alkyl group contains 8 or 9 carbon atoms, however, do not require a catalyst to react with water.

The reaction mixture may be heated to a suitable temperature to liquify a solid or semi solid reaction product.

The reaction mixture can optionally contain 1 to 25% by weight of and preferably 10% by weight of a hydrophobic isocyanate capped polyester diol (functionality 2). A preferred isocyanate capped polyester diol is derived from a polypropylene adipate of average molecular weight 500 to 2000 and 4,4-dicyclohexyl methane di-isocyanate (Desmodur W available from Bayer AG). The preferred isocyanate capped polyester diol can be prepared by mixing the diol and diisocyanate compounds with 0.2% weight of dibutyl tin dilaurate in a suitable container and heating the mixture for example to a temperature of 90° C. for approximately two hours.

In the process of the invention water or an aqueous solution will normally be provided in liquid form which is mixed and reacted with the reaction product. The water in the process, however, can also be provided by a material such as a metal salt hydrate which release water in liquid or vapour form when heated. Suitable metal hydrates for use in the invention includes $Na_2B_4O_7.10H_2O$, $Na_2SO_4.10H_2O$, $Na_2SiO_3.9H_2O$ and $MgSO_4.7H_2O$ which is preferred. In the process the metal salt hydrate which is preferably in particulate form is mixed into the reaction product. The mixture can then be heated to a suitable temperature to release the water for reaction with the reaction product.

The use of a metal salt hydrate in the process of the invention to provide the water for reaction with the reaction product can be advantageous in the preparation of stiff compressible foams of the invention. The reaction product used in the preparation of these foams is normally solid at ambient room temperature and has to be heated to a temperature in the region of 60° C. to make it liquid. It has been found, however, in a process which uses water in liquid form that the rapid rate of reaction of the liquid reaction product with water at this temperature does not allow sufficient time to obtain a good dispersion of the water in the reaction product which results in a non-uniformly expanded foam being obtained.

The process of forming a uniform stiff foam of the invention can simply be achieved, however, by selecting a metal salt hydrate which releases water at a temperature well above that at which the reaction product becomes liquid, mixing the metal salt hydrate into liquid reaction product and heating the mixture to a temperature at which the metal salt hydrate reaction water.

The use of a metal salt hydrate in the process of the invention has a further advantage in that, because good mixing of the metal hydrate in the reaction product can be obtained, the amount of water provided by the metal salt hydrate need only be the stoichiometric amount needed for reaction with the reaction product.

The foam can be formed into a sheet or a desired shape by casting the foaming mixture into a release carrier or into a shaped mould and allowing the mixture to rise and set. The process of the invention allows the production of both flexible and stiff foams. A stiff foam for example in the form of sheet can be compressed by passage through nip rollers.

The foams produced by the process of the invention can then be incorporated into absorptive devices using conventional methods.

The invention will now be illustrated by reference to the following examples.

EXAMPLES 1 TO 6

Examples 1 to 6 describe the preparation of reaction products of the invention formed from a polyethylene glycol (PEG) mono lauryl ether and an aliphatic polyisocyanate. The reaction products were prepared by the general method given below.

The PEG mono lauryl ether (Brij 30 or 35) and aliphatic polyisocyanate (Desmodur N100) components together with di butyl tin dilaurate (catalyst T12) in the required amounts were added to a wide neck glass jar if necessary heated to 25° C. to 30° C. to premelt the PEG mono lauryl ether, and stirred until homogeneous mixture was obtained. The mixture was further stirred until the reaction was complete as indicated by the subsiding exotherm. The reaction product so formed was stored under dry conditions for at least 24 hours prior to use.

The reaction components used in the preparation of the reaction products of Example 1 to 6 are given in the following table.

| Reaction Components | Example No. | | | | | |
|---|---|---|---|---|---|---|
| (% by wt.): | 1 | 2 | 3 | 4 | 5 | 6 |
| Brij 35 | 62.5 | 58.8 | 66.7 | 57.7 | 43.9 | |
| Brij 30 | | | | | | 23.2 |
| Desmodur N100 | 37.5 | 41.2 | 33.3 | 52.2 | 56.0 | 76.3 |
| Water | 0.05 | 0.05 | 0.05 | 0.10 | 0.10 | 0.5 |
| Catalyst T12 (% by weight of reactants) | 0.2 | 0.2 | 0.2 | 0.2 | 0.2 | 0.2 |
| NCO/OH ratio | 3.0 | 3.5 | 2.5 | 3.0 | 3.5 | 4.0 |
| Isocyanate functionality of reaction product | 2.0 | 2.5 | 1.5 | 2.0 | 2.5 | 3.0 |

The Brij 30 and 35 have a molecular weight of approximately 360 and 1020 respectively. The Brij components were first dried under vacuum to a residual water content of less than 0.1%. The water used in the reaction includes residual water in the Brij components and if necessary added water to the required amount.

EXAMPLES 7 TO 12

Hydrophilic foams of the invention were formed from the reaction products of examples 1 to 6 by the following general method.

The reaction product was heated to a temperature of 60° to 70° C. to reduce its melt viscosity and 10% by weight water mixed into the molten reaction product. The foaming mixture was then cast into a polytetrafluoroethylene lined mould and the mixture allowed to rise, gel and set to form a hydrophilic polyurethane foam of the invention.

The foams so formed had the following properties.

|  | Example No. | | | | | |
| --- | --- | --- | --- | --- | --- | --- |
|  | 7 | 8 | 9 | 10 | 11 | 12 |
| Example No. of reaction product used to form foam | 1 | 2 | 3 | 4 | 5 | 6 |
| Water absorption of foam (% by weight) | 91 | 91 | 82 | 80 | 91 | 67 |
| Water absorption of polymer (% by weight) | 73 | 63 | 64 | 52 | 60 | 31 |
| Foam Density (Kg/m$^3$) | 86 | 85 | 105 | 107 | 100 | 100 |

Water absorption of the polymer was obtained by weighing a 1 cm cube of the foam dry, immersing the foam in water for 24 hours, squeezing out the water absorbed by the foam and reweighing the squeezed foam. The water absorption (% by weight) of the polymer was then calculated as:

$$\frac{\text{weight of squeezed foam (g)} - \text{weight of dry foam (g)}}{\text{Weight of squeezed foam (g)}} \times 100$$

The hydrophilic polyurethane foams of Examples 7 to 12 were flexible open cell foams.

The foams of Examples 7 and 8 were found to be suitable for use as an absorbent component of a wound dressing.

The foams of Examples 9 to 11 were found to be suitable as an absorbent component in sanitary towels.

The foam of Example 12 was found to be suitable for use as a liquid transmission and distribution component in an incontinence pad.

EXAMPLE 13

A reaction product was formed in the same manner as Examples 1 to 6 using dried PEG monomethylether of molecular weight 550 (48.2% by weight), Desmodur N100 (51.8% by weight) and catalyst T12 (0.2% by weight). The amount of water in the reaction was 0.2% by weight. The molar NCO/OH ratio of the reactants was 2.5:1. The isocyanate functionality of the reaction product was 1.5.

The reaction product prepared above was then used to form a hydrophilic polyurethane foam of the invention in the same manner as Examples 7 to 12 except that the reaction product was mixed with 6% by weight of water and 0.5% of K$_2$CO$_3$ as a catalyst for the reaction.

The hydrophilic polyurethane foam so formed was a flexible open cell foam with a density of 96 Kg/m$^3$ and a water absorption of 86.9% by weight. The water absorption of the foam polymer was 41.7% by weight.

EXAMPLE 14

The example describes the preparation of a stiff compressible foam of the invention.

A reaction product was prepared in the same manner as Examples 1 to 6 using PEG mono methyl ether 5000 (56% by weight), Desmodur N100 (44% by weight) and catalyst T12 (0.2% by weight) except that the reactants were heated together at a temperature of 90° C. for 20 minutes. The amount of water present in the reaction was 1.0%.

The molar NCO/OH ratio of the reactants was 3:1. The isocyanate functionality of the reaction product was 2.0.

A hydrophilic polyurethane foam of the invention was prepared by mixing the reaction product (95.65% by weight) made molten by heating to a temperature of 60° C. with finely powdered Mg SO$_4$.7H$_2$O (4.35% by weight) that is sufficient to give a stoichiometric amount of water when heated. The mixture was transferred to a polytetrafluoroethylene lined mould and placed in an oven at 90° C. to cause the Mg SO$_4$.7H$_2$O to release water and react with the NCO groups. The foaming mixture was allowed to rise and set in the oven (approximately 5 minutes). The mould was then removed from the oven and the foam removed from the mould and cooled.

The hydrophilic polyurethane foam had a density of 100 kg/m$^3$ and a water absorption of 90% by weight. The water absorption of the foam polymer was 70% by weight. The foam was a relatively stiff open cell foam which was capable of being permanently compressed. A 1″ thick sheet of the foam was compressed to a thickness of 0.25″ by passage through nip rollers. The compressed sheet swelled to a thickness of 2.5 when immersed in water.

The foam of this example was found to be suitable as a swellable component of a sanitary absorptive device.

EXAMPLE 15

This example describes the preparation of a foam of the invention containing hydrophobic polyester units.

An isocyanate terminated polyester was formed by mixing 1 mole of polypropylene adipate of molecular weight 2000 with 2 moles of Desmodur W and 0.2% by weight of T12 catalyst and heating the mixture for 2 hours at 90° C.

The foams was prepared in the same manner as Examples 7 to 12 by mixing 9 parts of weight of the reaction product of Example 2 with 1 part by weight of the isocyanate terminated polyester prepared above and 1 part by weight of water. The foaming mixture was placed in polytetrafluoroethylene linked tray and allowed to rise and set. The hydrophilic polyurethane foam had a density of 76 Kg/m$^3$ and a water absorption of 94% by weight. The water absorption of the foam polymer was 43% by weight. The foam was found to have a better strength when hydrated than the foam of Example 8.

EXAMPLE 16

This example describes the preparation of a foam of the invention using a reaction product of polyethylene glycol nonyl phenyl ether and a polyisocyanate.

The reaction product was formed in the same manner as examples 1 to 6 using Antarox CO-520 (1 mole) Desmodur N 100 (3 moles) and catalyst T12 (0.2% by weight). The amount of water present in the reaction was 0.02% by weight. The molar NCO/OH ratio of the reactants was 3:1. The isocyanate functionality of the reaction product was 2.0. Antarox CO-520 used in the reaction is a polyethylene glycol mono nonyl phenyl ether of molecular weight of approximately 440.

The reaction product prepared above was then used to form a hydrophilic polyurethane foam of the invention by mixing the reaction product with 10% by weight of water in the same manner as Example 7 to 12.

The hydrophilic polyurethane foam so formed was a flexible open cell foam with a density of 55 Kg/m$^3$ and a water absorption of 54.7% by weight. The water absorption of the polymer was 12.2% by weight.

The hydrophilic polyurethane foam was found to be suitable for use in sanitary towels.

EXAMPLE 17

This example describes the preparation of a foam of the invention using the reaction product of a mixture of two polyethylene glycol mano ethers and two polyisocyanates.

The reaction product was formed in the same manner as Examples 1 to 6 using Brij 35 (0.667 moles), Antarox CO-520 (0.333 moles), Desmodur N 100 (2.0 moles) Suprasec DND (2.0 moles) and catalyst T12 (0.12% by weight). The amount of water present in the reaction was % by weight. The molar NCO/OH ratio of the reactants was 4:1.

The reaction product prepared above was then used to form a hydrophilic polyurethane foam of the invention by mixing the reaction product with 10% by weight of water in the same manner as Examples 7 to 12.

The hydrophilic polyurethane foam was found to be suitable for use as an absorbent component of sanitary towels.

EXAMPLES 18

This example describes the preparation of a foam of the invention using a reaction product of mixture of three polyethylene glycol monoethers, two polyisocyanates and a chain extender.

The reaction product was formed in the same manner as Example 17 using Brij 35 (0.70 moles), Antarox CO-520 (0.25 moles) 1,4 butane dial (0.60 moles) Desmodur N100 (4.4 moles) and Suprasec DND (4.4 moles) and catalyot T12 (0.12% by weight).

The reaction product prepared above was then used to form a hydrophilic polyurethane foam of the invention by mixing the reaction product with 10% by weight of water in the same manner as Example 17.

The hydrophilic polyurethane foam was found to be stiff enough to be used for a tampon.

We claim:

1. A hydrophilic polyurethane foam consisting essentially of residues of an isocyanate prepolymer, said isocyanate prepolymer being the product of the reaction of a polyisocyanate having a functionality of greater than 2 and a polyalkylene glycol monoalkyl ether, a polyalkylene glycol monoalkaryl ether or a mixture of such ethers and said foam having a polymer main chain consisting essentially of hydrophobic blocks provided by said isocyanate prepolymer and hydrophilic chains provided by said isocyanate prepolymer pendant to the polymer main chain.

2. A foam according to claim 1 wherein the ether is a polyethylene glycol monoalkyl or monoalkaryl ether.

3. A foam according to claim 1 wherein the ether is a mixture of said monoalkyl and monoalkaryl ethers.

4. A foam according to claim 1 wherein the ether is a polyethylene glycol monomethyl ether.

5. A foam according to claim 1 wherein the alkyl moiety of said monoalkyl group is from 10 to 18 carbon atoms.

6. A foam according to claim 5 wherein the alkyl moiety is cetyl or lauryl.

7. A foam according to claim 1 wherein the aryl moiety of the monoalkaryl group is phenyl.

8. A foam according to claim 7 wherein the alkyl moiety of the monoalkaryl group is octyl or nonyl.

9. A foam according to claim 1 wherein the ether has an average molecular weight of from 180 to 6000.

10. A foam according to claim 9 wherein the average molecular weight of the ether is from 350 to 1000.

11. A foam according to claim 9 wherein the average molecular weight of the foam is from 3000 to 5000.

12. A foam according to claim 1 wherein the polyisocyanate is an aliphatic isocyanate.

13. A process for the production of hydrophilic foams according to claim 1 which consists essentially of reacting (a) an isocyanate prepolymer obtained from the reaction of polyisocyanate having a functionality of greater than 2 and a polyalkylene glycol monoalkyl ether, a polyalkylene glycol monoalkaryl ether or a mixture of such ethers, with (b) water.

14. A process according to claim 13 wherein the water is derived from a substance which releases water when heated.

15. A process according to claim 14 wherein the substance is a metal salt hydrate.

16. A process according to claim 13, wherein said polyisocyanate has a functionality of greater than 2 to 5.

17. A process according to claim 13 wherein the amount of water ranges from the stoichiometric requirement to a 12% by weight excess of the stoichiometric requirement.

18. A process according to claim 13 wherein the ether is a polyethylene glycol monomethyl ether.

19. A process according to claim 13 which further comprises adding a catalytically effective amount of a catalyst.

20. A process according to claim 19 where the catalyst is potassium carbonate.

21. An absorptive device comprising a hydrophilic polyurethane foam according to claim 1.

22. A device according to claim 21 in the form of a wound dressing.

23. A device according to claim 21 in the form of a sanitary towel, diaper, incontinence pad or tampon.

24. A device according to claim 21, wherein said polyisocyanate has a functionality of greater than 2 to 5.

25. An absorptive medical dressing which comprises a polyurethane foam according to claim 1.

26. A dressing according to claim 25, wherein said polyisocyanate has a functionality of greater than 2 to 5.

27. A foam according to claim 1, wherein said polyisocyanate has a functionality of greater than 2 to 5.

28. A hydrophilic polyurethane foam consisting essentially of the reaction product of the reaction of (a) a prepolymer derived from the reaction of a polyalkylene glycol monoalkyl ether, a polyalkylene glycol monoalkaryl ether or a mixture of such ethers and a polyisocyanate having a functionality greater than 2 with (b) water.

29. A foam according to claim 28 wherein the ether is polyethylene glycol monoalkyl or monoalkaryl ether.

30. A foam according to claim 29 wherein the ether is selected from the group consisting of polyethylene glycol monomethyl ether, polyethylene glycol monocetyl ether, polyethylene glycol monolauryl ether, polyethylene glycol monooctylphenyl ether, polyethylene glycol monononyl phenyl ether and mixtures thereof.

31. A foam according to claim 28 wherein the polyisocyanate is an aliphatic isocyanate.

32. A hydrophilic polyurethane foam consisting essentially of the reaction product of the reaction of (a) an isocyanate prepolymer obtained from the reaction of an polyisocyanate having a functionality of greater than 2, and a polyalkylene glycol monoalkyl ether, a polyalkylene glycol monoalkaryl ether or a mixture of such ethers, (b) from 1 to 25% by weight of the reaction mixture of a hydrophobic isocyanate capped polyester diol and (c) water.

33. A foam according to claim 32 wherein the ether is a polyethylene glycol monoalkyl or monoalkaryl ether.

34. A foam according to claim 33 wherein the ether is selected from the group consisting of polyethylene glycol monomethyl ether, polyethylene glycol monocetyl ether, polyethylene glycol monolauryl ether, polyethylene glycol monooctylphenyl ether, polyethylene glycol monononyl phenyl ether and mixtures thereof.

35. A foam according to claim 32 wherein the isocyanate is an aliphatic isocyanate.

36. A foam according to claim 32, wherein said polyisocyanate has a functionality of greater than 2 to 5.

37. An absorptive device comprising a hydrophilic polyurethane consisting essentially of residues derived from an isocyanate prepolymer; said prepolymer being the product of the reaction of a polyisocyanate having a functionality of greater than 2 and a polyalkylene glycol monoalkyl ether, a polyalkylene glycol monoalkaryl ether or a mixture of such ethers; and from 1 to 25% by weight of the reaction mixture of a hydrophobic isocyanate capped polyester diol.

38. A device according to claim 37 in the form of a wound dressing.

39. A device according to claim 37 in the form of a sanitary towel, diaper, incontinence pad or tampon.

40. A device according to claim 37, wherein said polyisocyanate has a functionality of greater than 2 to 5.

41. An isocyanate prepolymer consisting essentially of product of the reaction of an aliphatic polyisocyanate having a functionality of greater than 2 and a polyethylene glycol monoalkyl ether, a polyalkylene glycol monoalkaryl ether or a mixture of such ethers.

42. A prepolymer according to claim 41 which further comprises residues of a chain extender.

43. A prepolymer according to claim 41 wherein the ether is a mixture of polyalkylene glycol monoalkyl ethers or a mixture of polyalkylene glycol monoalkaryl ethers.

44. A prepolymer according to claim 41, wherein said polyisocyanate has a functionality of greater than 2 to 5.

45. A hydrophilic polyurethane foam comprising residues of a polyalkylene glycol mono alkyl or alkaryl ether and residues of both an aromatic isocyanate and a aliphatic isocyanate.

46. The foam according to claim 45, wherein said aliphatic isocyanate is a biuret of 1,6-hexamethylene diisocyanate and said aromatic isocyanate is a polymeric methylene diisocyanate comprising a mixture 4,4'-diphenyl methane diisocyanates.

47. The foam according to claim 46, wherein said aliphatic isocyanate has a functionality of 2.6 and said aromatic isocyanate has a functionality of 2.7.

48. A wound dressing comprising a hydrophilic polyurethane foam comprising residues of a polyalkylene glycol mono alkyl or alkaryl ether and residues of both an aromatic isocyanate and an aliphatic isocyanate.

49. The wound dressing according to claim 48, wherein said aliphatic isocyanate is a biuret of 1,6-hexamethylene diisocyanate and said aromatic isocyanate is a polymeric methylene diisocyanate comprising a mixture 4,4'-diphenyl methane diisocyanates.

50. The wound dressing according to claim 49, wherein said aliphatic isocyanate has a functionality of 2.6 and said aromatic isocyanate has a functionality of 2.7.

51. A hydrophilic polyurethane foam consisting essentially of residues derived from an isocyanate prepolymer; said prepolymer being the product of the reaction of a polyisocyanate having a functionality of greater than 2 and a polyalkylene glycol monoalkyl ether, a polyalkylene glycol monoalkaryl ether or a mixture of such ethers; and from 1 to 25% by weight of the reaction mixture of a hydrophobic isocyanate capped polyester diol.

52. A process for the production of hydrophilic foams according to claim 51, which consists essentially of reacting (a) an isocyanate prepolymer obtained from the reaction of a polyisocyanate having a functionality of greater than 2 and a polyalkylene glycol monoalkyl ether, a polyalkylene glycol monoalkaryl ether or a mixture of such ethers, (b) from 1 to 25% by weight of the reaction mixture of a hydrophobic isocyanate capped polyester diol, and (c) water.

53. A process according to claim 52 wherein the isocyanate is an aliphatic isocyanate.

54. A process according to claim 53 wherein the isocyanate is 1,6 hexamethylene diisocyanate or a biuret thereof.

55. A foam according to claim 51, wherein said polyisocyanate has a functionality of greater than 2 to 5.

* * * * *